US005916787A

United States Patent [19]
Ingram et al.*

[11] Patent Number: 5,916,787
[45] Date of Patent: Jun. 29, 1999

[54] ETHANOL PRODUCTION IN GRAM-POSITIVE MICROBES

[75] Inventors: Lonnie O'Neal Ingram; Maria D. F. Barbosa-Alleyne, both of Gainesville, Fla.

[73] Assignee: Univeristy of Florida

[ * ] Notice: This patent is subject to a terminal disclaimer.

[21] Appl. No.: 08/475,925

[22] Filed: Jun. 7, 1995

Related U.S. Application Data

[63] Continuation of application No. 08/220,072, Mar. 30, 1994, Pat. No. 5,482,846, which is a continuation-in-part of application No. 08/026,051, Mar. 5, 1993, Pat. No. 5,554,520, which is a continuation-in-part of application No. 07/946,290, Sep. 17, 1992, Pat. No. 5,487,989, said application No. 08/026,051, is a continuation-in-part of application No. 07/846,344, Mar. 6, 1992, Pat. No. 5,424,202, which is a continuation-in-part of application No. 07/670,821, Mar. 18, 1991, abandoned, and application No. 07/624,227, Dec. 7, 1990, abandoned, said application No. 07/670,821, and application No. 07/624,227, each is a continuation-in-part of application No.07/352,062, May 15, 1989, Pat. No. 5,000,000, which is a continuation-in-part of application No. 07/239,099, Aug. 31, 1988, abandoned.

[51] Int. Cl.$^6$ .............................. C12P 7/06; C12P 7/08; C12N 1/20; C12N 15/00

[52] U.S. Cl. ................... 435/161; 435/163; 435/252.31; 435/320.1; 435/162; 435/165

[58] Field of Search ................................. 435/161, 163, 435/252.31, 252.3, 320.1, 165, 162

[56] References Cited

U.S. PATENT DOCUMENTS

| | | | |
|---|---|---|---|
| 5,482,846 | 1/1996 | Ingram et al. | 435/161 |
| 5,554,520 | 9/1996 | Fowler et al. | 435/165 |

OTHER PUBLICATIONS

Beall, D.S., L.O. Ingram (1993) "Genetic Engineering of Soft–rot Bacteria for Ethanol Production from Lignocellulose" J. Ind. Microbiol. 11:151–155.

Bräu, B., H. Sahm (1986) "Cloning and expression of the structural gene for pyruvate decarboxylase of *Zymomonas mobilis* in *Escherichia coli*" Arch. Microbiol 144:296–301.

Bringer–Meyer, S. et al. (1986) "Pyruvate decarboxylase from *Zymomonas mobilis*. Isolation and partial characterization" Arch Microbiol 146:105–110.

Conway, T. et al. (1987) "Cloning and Sequencing of the Alcohol Dehydrogenase II Gene from *Zymomonas mobilis*" Journal of Bacteriology 169(6): 2591–2597.

Gong, C–S et al. (1981) "Production of Ethanol from D–Xylose by Using D–Xylose Isomerase and Yeasts" Applied and Environmental Microbiology 41(2): 430–436.

Ingram, L.O., T. Conway (1988) "Expression of Different Levels of Ethanologenic Enzymes from *Zymomonas mobilis* in Recombinant Strains of *Escherichia coli*" Applied and Environmental Microbiology 54(2): 397–404.

Ingram, L.O. et al. (1987) "Genetic Engineering of Ethanol Production in *Escherichia coli*" Applied and Environmental Microbiology 53(10): 2420–2425.

Koide, Y. et al. (1986) "Cloning and Sequencing of the Major Intracellular Serine Protease Gene of *Bacillus subtilis*" Journal of Bacteriology 167(1): 110–116.

Mistry, F.R., C.L. Cooney (1989) "Production of Ethanol by *Clostridium thermosaccharolyticum*: I. Effect of Cell Recycle and Environmental Parameters" Biotechnology and Bioengineering 34:1295–1304.

Mistry, F.R., C.L. Cooney (1989) "Production of Ethanol by *Clostridium thermosaccharolyticum*: II. A Quantitative Model Describing Product Distributions" Biotechnology and Bioengineering 34:1305–1320.

Neale, A.D. et al. (1987) "Nucleotide sequence of the pyruvate decarboxylase gene from *Zymomonas mobilis*" Nucleic Acids Research 15(4): 1753–1761.

O'Hara, M.B., J.H. Hageman (1990) "Energy and Calcium Ion Dependence of Proteolysis during Sporulation of *Bacillus subtilis* Cells" Journal of Bacteriology 172(8): 4161–4170.

Sarthy, A.V. et al. (1987) "Expression of the *Escherichia coli* Xylose Isomerase Gene in *Saccharomyces cerevisiae*" Applied and Environmental Microbiology 53(9):1996–2000.

Tolan, J.S., R.K. Finn (1987) "Fermentation of D–Xylose and L–Arabinose to Ethanol by *Erwinia chrysanthemi*" Applied and Environmental Microbiology 53(9): 2033–2038.

Tolan, J.S., K. Finn (1987) "Fermentation of D–Xylose to Ethanol by Genetically Modified *Klebsiella planticola*" Applied and Environmental Microbiology 53(9): 2039–2044.

Wood, B.E., L.O. Ingram (1992) "Ethanol Production from Cellobiose, Amorphous Cellulose, and Crystalling Cellulose by Recombinant *Klebsiella oxytoca* Containing Chromosomally Integrated *Zymomonas mobilis* Genes for Ethanol Production and Plasmids Expressing Thermostable Cellulase Genes from *Clostridium thermocellum*" Applied and Environmental Microbiology 58(7): 2103–2110.

(List continued on next page.)

*Primary Examiner*—Rebecca E. Prouty
*Assistant Examiner*—Tekchand Saidha
*Attorney, Agent, or Firm*—Lahive & CockfieldLLP; Elizabeth A. Hanley; Linda M. Chinn

[57] ABSTRACT

The subject invention concerns the transformation of Gram-positive bacteria with heterologous genes which confer upon these microbes the ability to produce ethanol as a fermentation product. Specifically exemplified is the transformation of bacteria with genes, obtainable from *Zymomonas mobilis*, which encode pyruvate decarboxylase and alcohol dehydrogenase.

18 Claims, 2 Drawing Sheets

OTHER PUBLICATIONS

Danilevich, V.N. et al. (1994) "Construction of Recombinant Plasmids for Effective Expression of the Pyruvate Decarboxylase Gene from *Zymomonas mobilis* in *Bacillus subtilis* Cells" Molecular Biology 28:158–166.

Coleman, R.D. et al. (1987) "Cloning of the Debranching–Enzyme Gene from *Thermoanaerobium brockii* into *Escherichia coli* and *Bacillus subtilis*" Journal of Bacteriology 169(9):4302–4307.

Panbangred, W. et al. (1985) "Expression of a xylanase gene of *Bacillus pumilus* in *Escherichia coli* and *Bacillus subtilis*" Appl. Microbiol. Biotechnol. 22:259–264.

Hashiba, H. et al. (1992) "Establishment of a Host–vector System in *Lactobacillus helveticus* with β–Galactosidase Activity as a Selection Marker" Biosci. Biotech. Biopchem. 56(2):190–194.

Barbosa, M. de. F.S., L.O. Ingram (1994) "Expression of the *Zymomonas mobilis* Alcohol Dehydrogenase II (adhB) and Pyruvate Decarboxylase (pdc) Genes in Bacillus" Current Microbiology 28:279–282.

Gold, R.S. et al. (1992) "Ethanol tolerance and carbohydrate metabolism in lactobacilli" Journal of Industrial Microbiology 10:45–54.

Brock, T.D. et al. (1984) "Bergey's Classification of Bacteria" Biology of Microorganisms, 4th Edition, Appendix 4, 803–805.

Sneath, P.H.A. et al. (1986) Bergey's Manual of Systematic Bacteriology, vol. 2, Contents, xxi–xxiii.

ETHANOL PRODUCTION IN GRAM-POSITIVE MICROBES

CROSS-REFERENCE TO RELATED APPLICATIONS

This application is a continuation of application Ser. No. 08/220,072 (filed Mar. 30, 1994), now U.S. Pat. No. 5,482,846; which is a continuation-in-part of application Ser. No. 08/026,051 (filed Mar. 5, 1993), now U.S. Pat. No. 5,554,520; which is a continuation-in-part of application Ser. No. 07/946,290 (filed Sep. 17, 1992) now U.S. Pat. No. 5,487,989. Ser. No. 08/026,051 is also a continuation-in-part of application Ser. No. 07/846,344 (filed Mar. 6, 1992) now U.S. Pat. No. 5,424,202; which is a continuation-in-part of application Ser. No. 07/670,821 (filed Mar. 18, 1991), now abandoned, and application Ser. No. 07/624,227 (filed Dec. 7, 1990), now abandoned; both of which are continuations-in-part of application Ser. No. 07/352,062 (filed May 15, 1989), now U.S. Pat. No. 5,000,000 itself which is a continuation-in-part of application Ser. No. 07/239,099 (filed Aug. 31, 1988), now abandoned.

This research was supported in part by Grant Nos. 92-37308-7471 and 583620-2-112 from the Department of Agriculture and Grant No. FG05-86ER3574 from the Division of Energy Biosciences in the Department of Energy.

BACKGROUND OF THE INVENTION

During glycolysis, cells convert simple sugars, such as glucose, into pyruvic acid, with a net production of ATP and NADH. In the absence of a functioning electron transport system for oxidative phosphorylation, at least 95% of the pyruvic acid is consumed in short pathways which regenerate $NAD^+$, an obligate requirement for continued glycolysis and ATP production. The waste products of these $NAD^+$ regeneration systems are commonly referred to as fermentation products.

In most animals and plants as well as bacteria, yeast, and fungi, glucose is degraded initially by an anaerobic pathway prior to either oxidative or fermentative metabolism. The most common such pathway, termed glycolysis, refers to the series of enzymatic steps whereby the six-carbon glucose molecule is broken down, via multiple intermediates, into two molecules of the three carbon compound, pyruvate. During this process, two molecules of $NAD^+$ are reduced to form NADH. The net reaction in this transformation of glucose into pyruvate is:

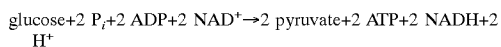

For glycolysis to continue, the $NAD^+$ consumed by glycolysis must be regenerated by the oxidation of NADH. During oxidative metabolism, NADH typically is oxidized by donating hydrogen equivalents via a series of steps to oxygen, thereby forming water. Most organisms contain additional anaerobic pathways, however, which allow glycolysis to continue in the absence of compounds like oxygen. Such anaerobic processes are termed fermentation, and homolactic fermentation is perhaps one of the most common of these pathways occurring in many bacteria and in animals. In homolactic fermentation, glucose ultimately is converted to two molecules of the three-carbon acid, lactic acid.

Ethanologenic organisms like *Zymomonas mobilis* and *Saccharomyces cerevisiae* are capable of a second (alcoholic) type of fermentation whereby glucose is metabolized to two molecules of ethanol and two molecules of $CO_2$.

Alcoholic fermentation differs from lactic acid fermentation in the steps used for the regeneration of $NAD^+$. Two different enzymatic steps are required for alcoholic fermentation. Pyruvate decarboxylase cleaves pyruvate into acetaldehyde and carbon dioxide. Alcohol dehydrogenase serves to regenerate $NAD^+$ by transferring hydrogen equivalents from NADH to acetaldehyde, thereby producing ethanol. The reactions for the regeneration of $NAD^+$ by alcoholic fermentation are:

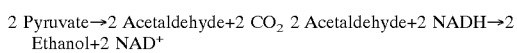

The net reaction for alcoholic fermentation is:

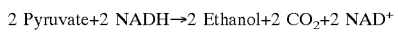

Pentose sugars, which can also be converted to ethanol, are abundant in nature as a major component of lignocellulosic biomass. One such pentose sugar is xylose, which is second only to glucose in natural abundance. Thus, as with hexose sugars, pentose sugars such as xylose can be converted into pyruvate by modified glycolytic pathways. The pyruvate can then be redirected to ethanol. The net reaction for a pentose sugar is typically: three pentose sugars yield five ethanol and five carbon dioxide molecules. Because of the abundance of pentose sugars, the fermentation of xylose and other hemicellulose constituents is an attractive option for the development of an economically viable process to produce ethanol from biomass. However, no naturally occurring microorganisms have been found which rapidly and efficiently ferment pentoses to high levels of ethanol. Yeasts such as *Pachysolen tannophilus, Candida shehatae,* and *Pichia stipitis* have been investigated as candidates for xylose fermentation. Efficient fermentation by these pentose-fermenting yeasts has proven difficult due to a requirement for oxygen during ethanol production, acetate toxicity, and the production of xylitol as a by-product. Other approaches to xylose fermentation include the conversion of xylose to xylulose using xylose isomerase prior to fermentation by *Saccharomyces cerevisiae* (Gong et al., 1981) and the development of genetically engineered strains of *S. cerevisiae* which express xylose isomerase (Sarthy et al., 1987). The thermophilic bacterium, *Clostridium thermosaccharolyticum,* represent an alternative and promising approach to xylose fermentation (Mistry and Cooney, 1989 [p. 1295]; Mistry and Cooney, 1989 [p. 1305]). High volumetric productivities have been achieved in continuous culture although final ethanol concentrations remained low.

Microorganisms are particularly diverse in the array of fermentations products which are produced by different genera (Krieg, N. R., and J. G. Holt, eds. [1984] *Bergey's manual of systematic bacteriology,* The Williams & Wilkins Co., Baltimore). These products include organic acids, such as lactic, acetic, succinic, and butyric, as well as neutral products, such as ethanol, butanol, acetone, and butanediol. Indeed, the diversity of fermentation products from bacteria has led to their use as a primary determinant in taxonomy (Krieg and Holt [1984], supra).

End products of fermentation share several fundamental features. They are relatively nontoxic under the conditions in which they are initially produced but become more toxic upon accumulation. The microbial production of these fermentation products forms the basis for our oldest and most economically successful applications of biotechnology and includes dairy products, meats, beverages, and fuels. In recent years, many advances have been made in the field of biotechnology as a result of new technologies which enable researchers to selectively alter the genetic makeup of some microorganisms. The invention described here relates to the use of recombinant DNA technology to elicit the production of specific useful products by a modified host.

The DNA used to modify the host of the subject invention can be obtained from *Zymomonas mobilis*. *Z. mobilis* is a microorganism which is commonly found in plant saps and in honey, and which has unusual metabolic characteristics. *Z. mobilis* has long served as a natural inocula for the fermentation of the Agave sap to produce pulque (an alcohol-containing Mexican beverage) and as inocula for palm wines. This organism is also used for fuel ethanol production and has been reported capable of ethanol production rates which are substantially higher than that of yeasts.

Although *Z. mobilis* is nutritionally simple and capable of synthesizing amino acids, nucleotides and vitamins, the range of sugars metabolized by this organism is very limited and normally consists of glucose, fructose and sucrose. *Z. mobilis* is incapable of growth even in rich medium such as nutrient broth without a fermentable sugar.

Like the yeast *Saccharomyces cerevisiae*, *Z. mobilis* produces ethanol and carbon dioxide as principal fermentation products. *Z. mobilis* produces ethanol by a short pathway which requires only two enzymatic activities: pyruvate decarboxylase and alcohol dehydrogenase. Pyruvate decarboxylase is the key enzyme in this pathway which diverts the flow of pyruvate to ethanol. Pyruvate decarboxylase catalyzes the nonoxidative decarboxylation of pyruvate to produce acetaldehyde and carbon dioxide. Two alcohol dehydrogenase isozymes are present in this organism and catalyze the reduction of acetaldehyde to ethanol during fermentation, accompanied by the oxidation of NADH to $NAD^+$. Although bacterial alcohol dehydrogenases are common in many organisms, few bacteria have pyruvate decarboxylase. Attempts to modify *Z. mobilis* to enhance its commercial utility as an ethanol producer have met with very limited success.

Most fuel ethanol is currently produced from hexose sugars derived from corn starch or cane syrup utilizing either *S. cerevisiae* or *Z. mobilis*. However, these are relatively expensive sources of biomass sugars and have competing value as foods. Starches and sugars represent only a fraction of the total carbohydrates in plants. The majority of the world's cheap, renewable source of biomass is not found as monosaccharides but rather in the form of lignocellulose, which is primarily a mixture of cellulose, hemicellulose, and lignin. The dominant forms of plant carbohydrate in stems, leaves, hulls, husks, cobs, etc. are the structural wall polymers, cellulose and hemicellulose. Hydrolysis of these polymers releases a mixture of neutral sugars which include glucose, xylose, mannose, galactose, and arabinose. Cellulose is a homopolymer of glucose, while hemicellulose is a more complex heteropolymer comprised not only of xylose, which is its primary constituent, but also of significant amounts of arabinose, mannose, glucose, and galactose. No single organism has been found in nature which can rapidly and efficiently metabolize these sources of biomass into ethanol or any other single product of value.

It has been estimated that microbial conversion of the sugar residues present in waste paper and yard trash from U.S. landfills could provide over ten billion gallons of ethanol. While microorganisms such as those discussed above can ferment efficiently the monomeric sugars which make up the cellulosic and hemicellulosic polymers present in lignocellulose, the development of improved methods for the saccharification of lignocellulose remains a major research goal.

Current methods of saccharifying lignocellulose include acidic and enzymatic hydrolyses. Acid hydrolysis usually requires heat and presents several drawbacks, including the use of energy, the production of acidic waste, and the formation of toxic compounds which can hinder subsequent microbial fermentations. Enzymatic hydrolysis thus presents a desirable alternative. For example, enzymes can be added directly to the medium containing the lignocellulosic material while microorganisms are growing therein.

Genetic-engineering approaches for the addition of saccharifying traits to microorganisms for the production of ethanol or lactic acid have been directed at the secretion of high enzyme levels into the medium. That is, the art has concerned itself with modifying microorganisms already possessing the requisite proteins for transporting cellularly-produced enzymes into the fermentation medium, where those enzymes can then act on the polysaccharide substrate to yield mono- and oligosaccharides. This approach has been taken because the art has perceived difficulty in successfully modifying organisms lacking the requisite ability to transport such proteins.

The genes encoding alcohol dehydrogenase II and pyruvate decarboxylase in *Z. mobilis* have been separately cloned, characterized, and expressed in *E. coli*. See Bräu & Sahm (1986a) *Arch. Microbiol.* 144:296–301, (1986b) *Arch. Microbiol.* 146:105–110; Conway et al. (1987a) *J. Bacteriol.* 169:2591–2597; Neale et al. (1987) *Nucleic Acids Res.* 15:1752–1761; Ingram and Conway [1988] *Appl. Environ. Microbiol.* 54:397–404; Ingram et al. (1987) *Appl. Environ. Microbiol.* 53:2420–2425.

Bräu and Sahm (1986a), supra, first demonstrated that ethanol production could be increased in recombinant *E. coli* by the over-expression of *Z. mobilis* pyruvate decarboxylase although very low ethanol concentrations were produced. Subsequent studies extended this work by using two other enteric bacteria, *Erwinia chrysanthemi* and *Klebsiella planticola*, and thereby achieved higher levels of ethanol from hexoses, pentoses, and sugar mixtures. See Tolan and Finn (1987) *Appl. Environ. Microbiol.* 53:2033–2038, 2039–2044. The genes encoding pyruvate decarboxylase (pdc) and alcohol dehydrogenase II (adhB) from *Zymomonas mobilis* have been expressed at high levels in Gram-negative bacteria, effectively redirecting fermentative metabolism to produce ethanol as the primary product (Beall et al., 1993; Ingram and Conway, 1988; Wood and Ingram, 1992).

Prior to our work, there has been no report of the transformation of Gram-positive bacteria to produce ethanol. The presence of multiple proteinases with overlapping specificities in Bacillus has been well established (Koide et al., 1986; O'Hara and Hageman, 1990) and may limit high level expression.

BRIEF SUMMARY OF THE INVENTION

The subject invention concerns the genetic transformation of Gram-positive bacteria with genes which confer upon these bacteria the capability of producing useful levels of ethanol. Specifically exemplified herein is the transformation of Bacillus sp. with heterologous genes which encode the pyruvate decarboxylase (pdc) and alcohol dehydrogenase (adh) enzymes. The expression of these heterologous genes results in the production of enzymes which redirect the metabolism of the transformed host such that ethanol is produced as a primary fermentation product of the host. The methods of the subject invention can be used to produce Gram-positive microorganisms that are capable of effectively diverting pyruvate to ethanol during growth under both aerobic and anaerobic conditions.

One advantageous embodiment of the subject invention employs the Z. mobilis genes encoding alcohol dehydrogenase and pyruvate decarboxylase in the recombinant host. Although these genes may be plasmid borne, a preferred embodiment of the subject invention involves the incorporation of these genes into the chromosome of the recombinant host.

In another embodiment of the subject invention, the recombinant host, in addition to comprising the DNA encoding alcohol dehydrogenase and pyruvate decarboxylase, further comprises DNA encoding proteins which enable the host to transport and metabolize an oligosaccharide. The host expresses the DNA at a level such that the host produces ethanol as a primary fermentation product from the metabolism of the oligosaccharide.

In another embodiment of the subject invention, a recombinant host, as described above, further comprises the DNA necessary to produce one or more polysaccharases. The production of a polysaccharase by the host, and the subsequent release of that polysaccharase into the medium, reduces the amount of commercial enzyme necessary to degrade feedstock into fermentable monosaccharides and oligosaccharides.

The polysaccharase DNA can be native to the host, although more often the DNA will be foreign, i.e., heterologous. Advantageous polysaccharases include cellulolytic, xylanolytic, and starch-degrading enzymes. The polysaccharase can be at least partially secreted by the host, or it can be accumulated substantially intracellularly for subsequent release. Advantageously, intracellularly-accumulated enzymes which are thermostable, can be released when desired by heat-induced lysis. Combinations of enzymes can be encoded by the heterologous DNA, some of which are secreted, and some of which are accumulated.

Other modifications can be made to enhance the ethanol production of the recombinant bacteria of the subject invention. For example, the host can further comprise an additional heterologous DNA segment, the expression product of which is a protein involved in the transport of mono- and/or oligosaccharides into the recombinant host. Likewise, additional genes from the glycolytic pathway can be incorporated into the host. In such ways, an enhanced rate of ethanol production can be achieved.

Yet another aspect of the subject invention provides a method for reducing the accumulation of acidic metabolic products in a growth medium by employing the inventive transformed hosts to produce ethanol in the medium. Still another aspect provides a method for enhancing the production of functional proteins in a recombinant host comprising overexpressing an adhB gene, such as that found in Z. mobilis, in the host.

DETAILED DISCLOSURE OF THE INVENTION

Figure 1:
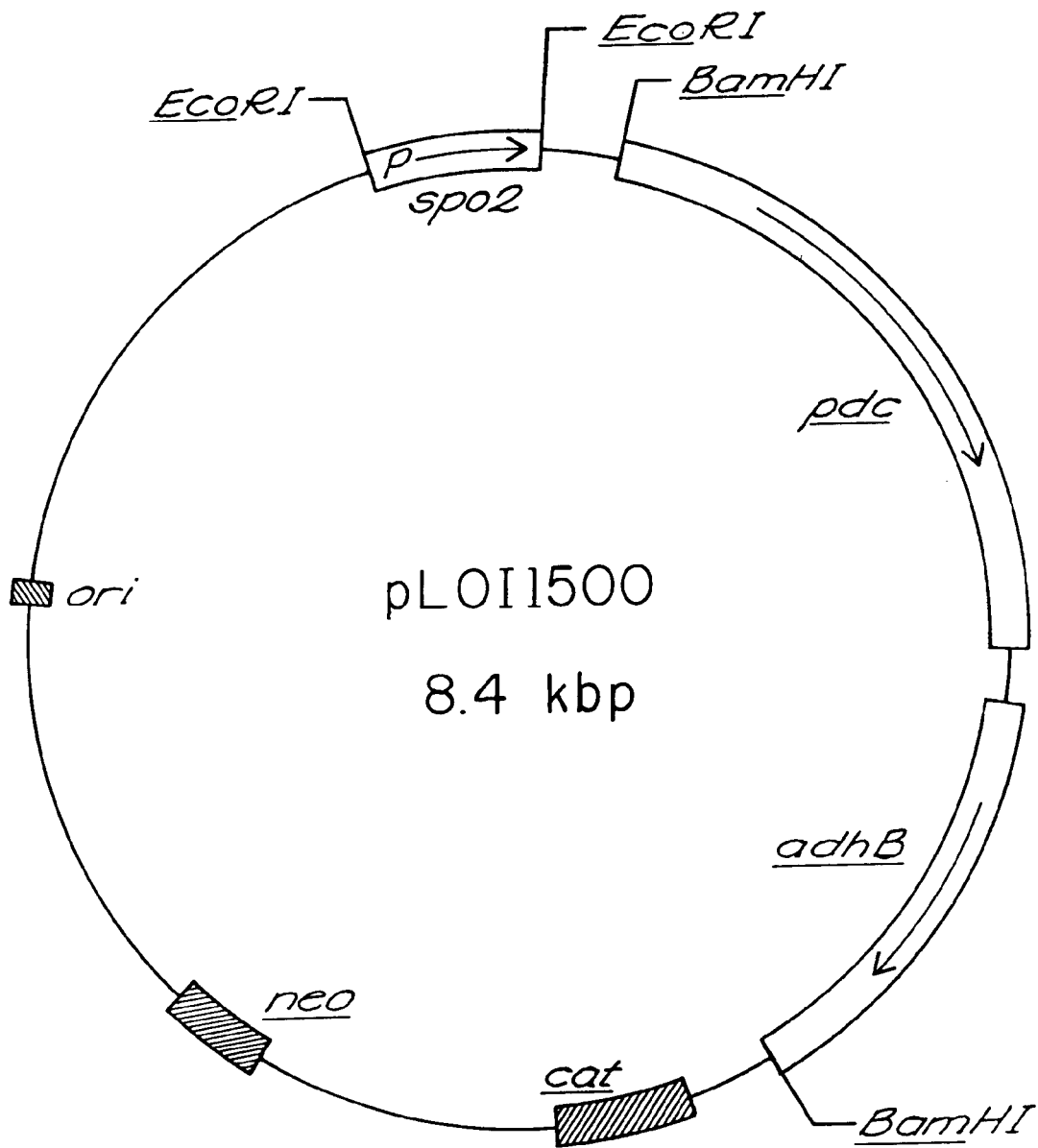
FIG. 1. Bacillus vector pLOI1500 for the expression of Z. mobilis pdc and adhB genes. The Z. mobilis genes are expressed under the control of a promoter (P) from phage SPO2.

The subject invention pertains to the genetic transformation of Gram-positive bacteria so as to provide these bacteria with the metabolic and enzymatic capabilities necessary for these bacteria to produce ethanol at useful levels. The invention described here allows the use of recombinant strains of Gram-positive bacteria for the production of ethanol from under-utilized sources of biomass, such as hemicellulose (xylose, arabinose, etc.), which represents a major portion of wood and inedible plant parts, and whey (lactose), as well as from other biomass sources.

According to the subject invention, Gram-positive organisms which carry out glycolysis, or some variant thereof, can be engineered to divert carbon flow from pyruvate glycolysis to a synthetic pathway comprised of the enzymes encoded by heterologous genes encoding pyruvate decarboxylase (pdc) and alcohol dehydrogenase (adh). The result is an engineered organism which produces ethanol as its primary fermentation product.

An important aspect of the present invention is an operon that directs cells to produce ethanol. Exemplary of such an operon is a construct of the present invention, designated a "pet operon," which can comprise Z. mobilis genes encoding alcohol dehydrogenase II and pyruvate decarboxylase activities together with appropriate regulatory sequences, for example, promoters, inducers, operators, ribosomal binding sites, and transcriptional terminators. Moreover, significant amounts of ethanol can be produced, in recombinants containing the pet operon, under both aerobic and anaerobic conditions.

In one embodiment of the subject invention, hosts can be selected which, by virtue of their native ability to transport and metabolize oligosaccharides, can ferment more complex feedstocks. In this context, "oligosaccharide" denotes a molecule comprised of two or more saccharide monomers, including but not limited to the disaccharides cellobiose, maltobiose, and xylotriose, trisaccharides like cellotriose and xylotriose, and long-chain polysaccharides such as cellulose, hemicellulose, starch, glycogen, pectin, and insulin. The capabilities of a host thus selected and transformed can be augmented by expression in the same host of one or more genes encoding a polysaccharase, i.e., an enzyme that catalyzes the breakdown to smaller oligosaccharides and/or saccharide monomers of complex oligosaccharides.

To impart to a microorganism the ability to produce polysaccharases, such as xylanases and cellulases, an ethanologenic operon of the present invention can be modified by adding the gene(s) which encode the desired enzyme(s). Alternatively, one or more polysaccharase-encoding genes can be incorporated into a plasmid which is used to transform a host organism already engineered with an operon that directs ethanol production, as described above. By yet another alternative approach, the host to be transformed with the ethanologenic operon is selected for its native ability to express a polysaccharase. Yet another approach is to add the polysaccharase genes into the chromosome by integration.

It is not necessary that the genes encoding alcohol dehydrogenase and pyruvate decarboxylase activities be under common control; they can be under separate control, even in different plasmids or in different locations on the chromosome. Likewise, gene(s) encoding polysaccharases can be under common or separate control, or located in different plasmids or at different chromosomal positions.

Another aspect of the present invention concerns the use of recombinant ethanol-producing hosts for the efficient production of recombinant peptides or proteins; that is, the recombinant cells can be transformed further with genes encoding useful products other than polysaccharases. These additional genes can be plasmid-borne or incorporated into the chromosome. More specifically, genes that encode the necessary ethanologenic enzymes generally are expressed at high levels and dominate carbon flow from pyruvate and NADH oxidation during anaerobic growth. Under these conditions, the flow of pyruvate carbon skeletons can be diverted from the production of organic acids to the production of ethanol as the principal fermentation product. In this way, the extent of acidification per unit of cell protein is minimized by the production of ethanol rather than organic acids.

Oxygen transfer is frequently a major limitation during the growth of dense cultures of microorganisms, and it is this limitation which results in acid production and pH drift of the growth medium. In recombinants expressing an ethanologenic operon according to the present invention, by contrast, the heterologous, ethanologenic enzymes divert part of the pyruvate from glycolysis to acetaldehyde and reoxidize NADH to produce ethanol, a less damaging product of metabolism. Thus, strains containing both functional respiratory chains for oxidative phosphorylation and ethanol production enzymes can be grown to even higher cell densities because of the operation of both systems during the regeneration of $NAD^+$ and a reduction in acidic waste products. Such inherent flexibility results in less stringent process-control requirements, as well as increased volumetric yields of recombinant products.

The accumulation of organic acids which otherwise occurs is regarded as a consequence of fermentation during anaerobic growth. But appreciable quantities of acetate may be produced even under aerobic conditions, e.g., during rapid agitation. Thus, the production of acetate may be progressive from the earliest stages of growth and not limited to the later stages, when cell density is high and anaerobic conditions prevail. Acid production from glucose, even under aerobic conditions, serves to limit growth in broth and on solid medium, as demonstrated by the increased final cell density in medium supplemented with phosphate buffer. Accordingly, ethanol-producing transformants within the present invention also are superior hosts for production of recombinant products, even under anaerobic conditions, with minimal acid production.

Many recombinant proteins and peptides contain cysteine or disulfide bridges, and proper folding or reactions of these is an essential feature to form the active enzyme. Since formation of disulfide bonds is promoted by oxygen, synthesis of such proteins under anaerobic conditions provides less opportunity for improper folding prior to isolation and folding under controlled conditions, thus resulting in greater recovery of biologically active product. The use of adhB in these constructs can be of particular advantage. AdhB encodes a stress protein (An et al., 1991). Stress proteins have been shown to aid in the proper folding of heterologous proteins allowing the retention of biological function (Lee et al., 1992). Accordingly, the use of adhB can enhance the production of functional proteins in recombinant organisms.

Foreign genes expressing enzymatic activity needed to redirect pyruvate metabolism, in accordance with the present invention, can be integrated into the chromosome and expressed without the need for a plasmid. For example, a pet construct which lacks a promoter can be integrated into the chromosome of the host immediately behind the promoter for the pyruvate formate lyase gene. Analogous integration into pfl or other genes is possible in most organisms, requiring only a fragment of the target gene to direct the site of integration by homologous recombination. Target genes other than pfl also can be used for integration. Since pet-expressing constructs are easily identified on indicator plates, this approach is readily utilized for the rapid and efficient construction of a variety of organisms for ethanol production.

A great many texts are available which describe procedures for expressing foreign genes. Also, catalogs list cloning vectors which can be used for various organisms including Gram-positive bacteria. Catalogs from which these cloning vectors can be ordered are readily available and well known to those skilled in the art. See, for example, Marino (1989) *BioPharm.* 2:18–33; *Vectors: A Survey of Molecular Cloning Vectors and Their Uses* (Butterworths 1988).

Genes useful according to the subject invention. As discussed above, Z. mobilis pdc and adh genes can be used according to the subject invention. The skilled practitioner also has access to alternative pdc and adh genes, and to other such genes which can be identified by use of the aforementioned Z. mobilis genes as probes or, more preferably, by observing activity on indicator plates. For purposes of this invention, it does not matter whether the alcohol dehydrogenase activity is provided from a gene isolated from a horse, yeast, human, insect, or other bacterial gene. Since expression of alcohol dehydrogenase activity can be observed directly on aldehyde indicator plates, sequence information would not be needed for the isolation of additional genes encoding proteins which exhibit this enzymatic activity. Indeed, many alcohol dehydrogenase genes are already well known to those skilled in the art, as evidenced by the recitation of 252 adh genes in the GenBank database as of March 1991 (IntelliGenetics, Inc., 700 E. El Camino Drive, Mountain View, Calif. 94040).

Z. mobilis contains two genes encoding functional alcohol dehydrogenase enzymes, and one of these (adhB) is related evolutionarily to a butanol dehydrogenase from *Clostridium acetobutylicum,* propanediol oxidoreductase from *E. coli,* and ADHIV alcohol dehydrogenase from Saccharomyces. All have been cloned and sequenced. The second alcohol dehydrogenase gene from Z. mobilis, adhA; is a zinc alcohol dehydrogenase which also has been cloned and sequenced. Based upon comparisons of primary structure deduced from sequences which are readily available, the adhA gene is deemed related evolutionarily to the typical alcohol dehydrogenases described in animals, plants, and the dominant adh gene in yeasts. The adhA gene and other alcohol dehydrogenase genes can be substituted for the original adhB gene exemplified herein.

By the same token, for purposes of this invention, it does not matter whether the pyruvate decarboxylase activity is provided by a gene from Z. mobilis or by a gene which encodes the needed enzymatic activity but which comes from corn, yeast, or some other organism. The evolution of life forms from common ancestry is now well accepted and has been demonstrated in splendid detail by the methods of molecular genetics. Not only can organisms be arranged in phylogenetic trees based on macro-characteristics, but the ancestral genes which have evolved for specific functions have been retained throughout evolution with conservation of features required for such functions. This high level of conservation enables those skilled in the art to isolate functionally equivalent, genetically related enzymes from other organisms using primary information from one or more members of an enzyme family. The enzymes of glycolysis are some of the best examples of this since such enzymes have been so well studied.

Indeed, just such an approach has been used successfully to clone the pyruvate decarboxylase gene from maize, using information on the Z. mobilis pdc and the pdc of S. cerevisiae to design a DNA probe. See Kelly (1989) *Plant Molecular Biology* 13:213–222. Alternative strategies can use the entire genes as probes. Since the synthesis of a protein with pyruvate decarboxylase activity (pyruvate converted to acetaldehyde plus carbon dioxide) can be observed directly on aldehyde indicator plates, sequence information is not needed to locate other genes, although sequence information has been used to isolate the corn gene. Many other pyruvate decarboxylase genes which provide a functional equivalent can be isolated from other organisms. These other genes are suitable replacements for the Z. mobilis pdc, just as several alcohol dehydrogenases have proven suitable. Further in that regard, the GenBank database listed at least 5 pdc genes as of March 1991.

Chromosomal integration of foreign genes. Chromosomal integration of foreign genes can offer several advantages over plasmid-based constructions, the latter having certain limitations for commercial processes. Ethanologenic genes have been integrated chromosomally in *E. coli* B; see Ohta et al. (1991) *Appl. Environ. Microbiol.* 57:893–900. In general, this is accomplished by purification of a DNA fragment containing (1) the desired genes upstream from a chloramphenicol gene and (2) a fragment of homologous DNA from the target organism. This DNA can be ligated to form circles without replicons and used for transformation. Thus, the pfl gene can be targeted in the case of *E. coli*, and short, random Sau3A fragments can be ligated in Klebsiella to promote homologous recombination.

Initial selections of recombinants can be made on 20 mg chloramphenicol ("Cm")/liter plates to allow growth after single copy integration. These constructs may be obtained at a very low frequency. Ethanologenic genes initially may be expressed at low levels, insufficient to permit efficient ethanol fermentation. Higher level expression may be achieved as a single step by selection on plates containing 600 to 1000 mg Cm/liter. Such strains have proven very stable. Testing of certain wild strains indicates that electroporation improves plasmid delivery and may reduce the effort required to achieve integrations.

Host selection. The range of organisms suitable for modification to express heterologous pdc and adh genes, as described above, includes, inter alia, eukaryotic cells, such as animal cells, insect cells, fungal cells, yeasts which are not naturally ethanologenic, and non-ethanologenic bacteria. Specifically exemplified herein are the Gram-positive bacteria. For example, the Gram-positive host according to the subject invention can be selected from the group consisting of Bacillus, Lactobacillus, Streptococcus, Fibribacter, Ruminococcus, Pediococcus, Cytophaga, Cellulomonas, Bacteroides, and Clostridium. Appropriate methodology for the introduction of foreign genes is available for each of these different types of hosts.

According to the present invention, pdc and adh genes can be introduced into a variety of different hosts and expressed using a variety of promoters. It is well within the skill of a person trained in this field to use the descriptions provided herein to make these constructions. For example, pdc and adh genes can be readily inserted into plasmids which have different host ranges. These vectors are available from catalogs and are well known to those skilled in the art.

A variety of factors should be considered in selecting host strains suitable for ethanol production pursuant to the present invention. These factors include substrate range and environmental hardiness, such as sugar tolerance, salt tolerance, ethanol tolerance, tolerance to low pH, and thermal tolerance.

Certain organisms among the aforementioned microbes also meet the criteria for selection of a host to ferment oligosaccharide(s) to ethanol in accordance with the present invention. More specifically, a host can be selected in this regard because it produces (1) the proteins necessary to transport an oligosaccharide into the cell and (2) intracellular (cytoplasmic) levels of enzymes which metabolize those oligosaccharides.

Hosts can be selected, in satisfaction of criteria (1) and (2), above, from Gram-positive bacteria, including members of the genera Bacillus, such as *B. pumilus, B. subtilis,* and *B. coagulans;* Clostridium, for example, *Cl. acetobutylicum, Cl. aerotolerans, Cl. thermocellum, Cl. thermohydrosulfuricum,* and *Cl. thermosaccharolyticum;* Cellumonas species like *C. fimi* and *C. uda;* and *Butyrivibrio fibrisolvens*.

Those skilled in this art will appreciate that many other hosts are suitable for use in the present invention. Thus, suitable hosts can be identified by screening to determine whether the tested microbe transports and metabolizes oligosaccharides. Screening in this vein can be accomplished in various ways. For example, microorganisms can be screened to determine which grow on suitable oligosaccharide substrates, the screen being designed to select for those microorganisms that do not transport only monomers into the cell. A preferred screen is to use an oligosaccharide as the sole source of carbon for growth in a minimal medium. Alternatively, one can test for the production of organic acids as products from the metabolism of oligosaccharides using either dyes as pH indicators or by using analytical methods (gas chromatography or high performance liquid chromatography) to measure for fermentation products. Another alternative is to test for gas production from oligosaccharides using Durham tubes or other methods known to those skilled in the art. Alternatively, microorganisms can be assayed for appropriate intracellular enzyme activity, e.g., β-glucosidase and β-xylosidase activity.

In one specific embodiment of the subject invention, the genes encoding *Zymomonas mobilis* pyruvate decarboxylase (pdc) and alcohol dehydrogenase II (adhB) were expressed in *Bacillus subtilis* YB886(pLOI1500) under the control of a Bacillus SPO2 phage promoter. Expression was further confirmed by Western blots, activity stains of native gels, and in vitro measurements of alcohol dehydrogenase activity. The results obtained demonstrated that there are no inherent barriers preventing the expression of *Z. mobilis* pdc and adhB genes as active enzymes in *B. subtilis* and *B. polymyxa*. Several promoters were tested with similar results. We also found that correctly-folded PDC and ADHII from *E. coli* appeared relatively resistant to proteolysis by YB886(pLOI1500) protein extracts in vitro. Additional strains of Bacillus were also transformed and all produced similar levels of these enzymes. These results establish that no fundamental barriers exist to the expression of these *Z. mobilis* genes in Bacillus. Two abundant new proteins (ca. mass 33,000 daltons and 14,000 daltons) were observed in Coomassie blue-stained gels which are similar in size to the proteins induced by recombinant products in *Escherichia coli*.

Those skilled in the art will appreciate that a number of modifications can be made to the methods and materials exemplified herein. For example, a variety of promoters can be utilized to drive expression of the heterologous genes in the Gram-positive recombinant host. The skilled artisan, having the benefit of the instant disclosure, will be able to readily choose and utilize any one of the various promoters available for this purpose. Similarly, skilled artisans, as a matter of routine preference, may utilize a higher copy number plasmid or, as described herein, chromosomal integration of the desired genes. Further optimization can be readily achieved by replacing the ribosomal binding site on the adh or pdc genes with a native ribosomal binding site from the Gram-positive host. Specifically, in the case of a Bacillus host, the operon can be modified to include the binding site from a Bacillus gene. Finally, it is a matter of routine laboratory practice to mutate with chemicals or radiation to create and select mutants with higher levels of expression. Aldehyde indicator plates or pyruvate decarboxylase activity stains can be conveniently used to identify strains with useful mutations.

A *Bacillus subtilis* host containing plasmid pLOI1500 was deposited with the American Type Culture Collection (ATCC), 12301 Parklawn Drive, Rockville, Md. 20852 USA. The culture was assigned the following accession number by the repository:

| Culture | Accession number | Deposit date |
|---|---|---|
| *Bacillus subtilis* rB886 (pLOI1500) | ATCC 69588 | March 14, 1994 |

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Materials and Methods

Bacterial strains, plasmids and growth conditions. The following *B. subtilis* strains were used: YB886 (Yasbin et al., 1980), 168 ISP (Koide et al., 1986), 36361SP (O'Hara and Hageman, 1990), 168 S-87 (Hageman, personal communication), and NRC9057 and NRC5990 (Baird et al., 1990). Other bacterial strains used in this study include *E. coli* DH5α (Bethesda Research Laboratories) and *B. polymyxa* NRC2882 (Baird et al., 1990). Plasmids pLOI292 and pLOI295 (Ingram and Conway, 1988) and pPL708 (Duvall et al., 1983) have been previously described. Cultures were routinely grown at 37° C. in Luria broth (Luria and Delbruck, 1943) supplemented with 50 g/l glucose or on Luria agar (15 g/l agar and 20 g/l glucose). Recombinants of *B. subtilis* and *B. polymyxa* were selected on Luria agar containing kanamycin (10 mg/l), and screened on aldehyde indicator plates for the expression of alcohol dehydrogenase activity (Ingram and Conway, 1988). Growth of all organisms was monitored at 550 nm with a Spectronic 70 spectrophotometer (Bausch & Lomb, Inc., Rochester, N.Y.).

DNA manipulations. Standard methods were used for the purification of plasmid DNA, plasmid construction, and transformation (Harwood and Sutting, 1991; Sambrook et al., 1989). *B. subtilis* NRC9057 was transformed by electroporation (Brigidi et al., 1990). Digestions with restriction enzymes were carried out as recommended by the manufacturers.

Gel electrophoresis and immunoblots. Soluble protein extracts were prepared as described previously (An et al., 1991) from cultures grown for 8 hours. Proteins were separated by sodium dodecyl sulfate-polyacrylamide gel electrophoresis (SDS-PAGE) essentially as described by Laemmli (1970) and either stained with Coomassie Brilliant Blue or electroblotted to nitrocellulose membranes for Western analysis (Aldrich et al., 1992; An et al., 1991). Zymograms of native polyacrylamide gels (8% acrylamide) were stained for ADHII (Williamson et al., 1980) and PDC (Zehender et al., 1983) activities.

Enzyme assays. The specific activities of PDC and ADHII were determined in cell free extracts as previously described (Ingram and Conway, 1988).

Following are examples which illustrate procedures, including the best mode, for practicing the invention. These examples should not be construed as limiting. All percentages are by weight and all solvent mixture proportions are by volume unless otherwise noted.

EXAMPLE 1—PLASMID CONSTRUCTION AND TRANSFORMATION

A promoterless pet operon was isolated as a 3.2 kilobase pair (kbp) BamHI fragment from pLOI292. This fragment was ligated into the BamHI site of the Bacillus expression vector, pPL708, under the control of the spo promoter (Schoner et al., 1983) to produce pLOI1500 (FIG. 1). To confirm that the *Z. mobilis* genes were not altered during construction or maintenance in *B. subtilis* YB886, the 3.2 kbp BamHI fragment was reisolated from YB886 (pLOI1500) and subcloned into pUC18 to produce pLOI1528. PDC and ADHII activities in *E. coli* DH5α (pLOI1528) (Table 1) were equivalent to those expressed by an analogous construct, pLOI295 (Ingram and Conway, 1988), the source of the pet operon for pLOI292.

TABLE 1

PDC and ADHII activities in recombinant strains of *E. coli* DH5α and *B. subtilis* YB886

| | Specific activity[a] | |
|---|---|---|
| | ADHII | PDC |
| *E. coli* DH5 | <0.01 | <0.01 |
| DH5α (pLOI292) | 0.81 | 0.94 |
| DH5α (pLOI1528)[b] | 3.6 | 2.9 |
| *B. subtilis* YB886 | <0.01 | nd[c] |
| YB886 (pLOI1500) | 0.17 | nd |

[a]Expressed as μmoles of substrate/minute per mg of protein, (12).
[b]3.2 kbp containing the pet operon subcloned from pLOI1500 into pUC18.
[c]Not determined.

EXAMPLE 2—EXPRESSION OF PROTEINS ENCODED BY *Z. MOBILIS* GENES

The expression of both *Z. mobilis* pdc and adhB was confirmed immunologically in colony lifts using polyclonal antisera (Aldrich et al., 1992). Western blots revealed the presence of full length subunits for both PDC and ADHII. Two new smaller proteins were observed in stained gels, ca. mass of 14,000 (14 K) and 33,000 (33 K) daltons. It is unlikely that these smaller proteins are degradation products of Z. mobilis enzymes since both failed to react with either polyclonal antibody. The 14 K and 33 K proteins were present only in YB886 recombinants which expressed the Z. mobilis genes. Deletion of the spo promoter (EcoRI fragment) to produce pLOI1503 eliminated their expression, the inhibition of growth, and the expression of the Z. mobilis genes in recombinant YB886.

A second higher molecular weight band was also detected in YB886(pLOI1500) with antisera to ADHII, an abundant Z. mobilis stress protein (An et al., 1991). This band was observed previously in recombinant E. coli harboring only Z. mobilis adhB and appears to represent an incompletely denatured dimeric form (Aldrich et al., 1992).

EXAMPLE 3—EXPRESSION OF FUNCTIONAL PDC AND ADHII

Figure 2A:
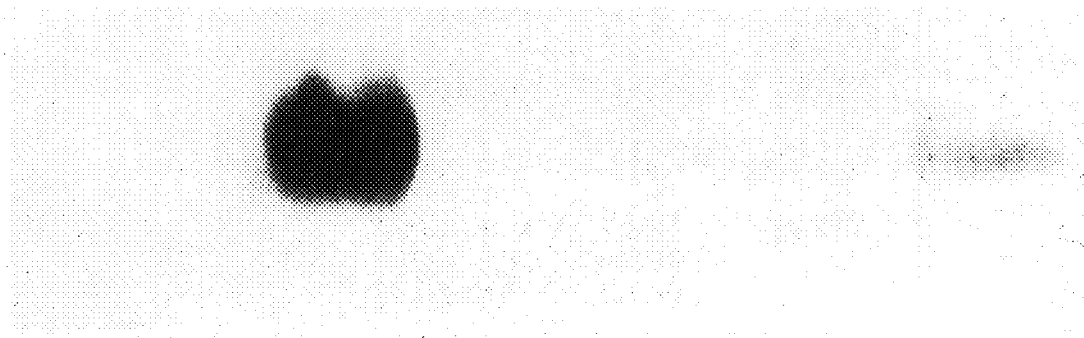
FIG. 2. Zymograms of native polyacrylamide gels (8%) stained for ADHII (A) and PDC (B) activities. Lanes: 1, E. coli DH5α; 2, E. coli DH5α(pLOI292); 3, B. subtilis YB886; 4, B. subtilis YB886(pPL708); 5, B. subtilis YB886 (pLOI1500). All lanes contained approximately 5 μg of protein.
Figure 2B:
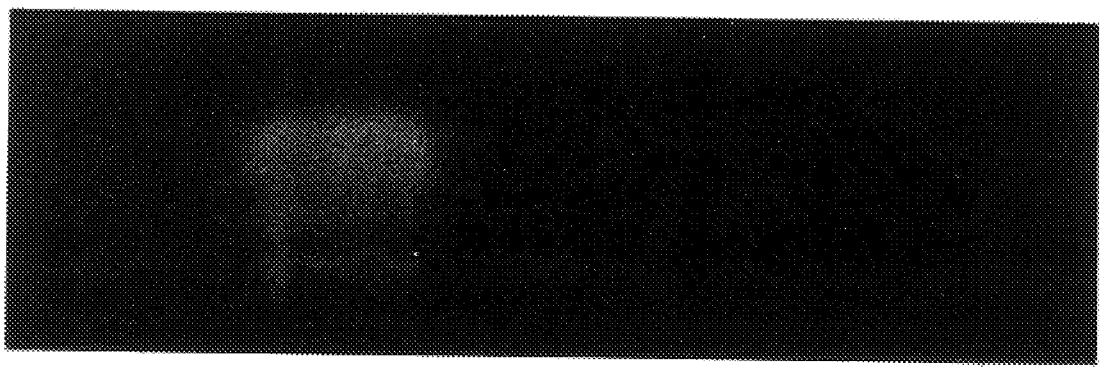

ADHII activity was readily measured in protein extracts from YB886(pLOI1500) (Table 1). PDC activity could not be determined in B. subtilis due to the high background levels of native, heat-stable lactate dehydrogenase (Conway et al., 1987). The expression of both Z. mobilis adhB and pdc as functional enzymes in YB886(pLOI1500) was confirmed by activity stains of native gels (FIG. 2 (A and B, respectively)).

Additional plasmids were constructed for expression of the Z. mobilis genes in YB886. The promoterless plasmid, pLOI1503, was used as a recipient for 1 to 3 kbp PstI fragments of YB886 chromosomal DNA as a source of native promoters. Although many positive clones were identified in colony lifts, none appeared more active than pLOI1500.

EXAMPLE 4—ALTERNATIVE HOSTS

Several additional strains of Bacillus were also tested as hosts. Successful transformations of pLOI1500 without rearrangement were achieved with B. polymyxa NRC2992, B. subtilis NRC5990, and B. subtilis NRC9057, among others. In all cases, PDC and ADHII activities were observed.

EXAMPLE 4—EFFECT OF PROTEINASES

To examine the possibility that native proteinases might prevent high expression of Z. mobilis genes, three mutant strains with proteinases mutations (strains 1681SP, 36361SP, and 168 S-87) were also transformed with pLOI1500. None produced higher levels of Z. mobilis gene products. Additional in vitro experiments were conducted to evaluate the potential role of proteinases. Soluble protein extracts from YB886(pLOI1500) were mixed and incubated with extracts from E. coli(pLOI292) containing PDC and ADHII. During a six hour incubation at 37° C., PDC and ADHII activities (estimated from zymograms) and proteins (Coomassie blue-stained native gels) remained essentially unchanged. After 24 hours, both enzymes were degraded to approximately the same extent as native B. subtilis YB886 proteins. The correctly folded PDC and ADHII proteins do not appear particularly sensitive to proteolysis. Indeed, the new 14 K and 33 K proteins observed in YB886 recombinants expressing pdc and adhB are similar in size to stress proteins induced by recombinant products in E. coli (Allen et al., 1992) which are proposed to be involved in proteolysis.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Aldrich, H. C., L. McDowell, M. D. F. S. Barbosa, L. P. Yomano, R. K. Scopes, L. O. Ingram (1992) "Immunocytochemical localization of glycolytic and fermentative enzymes in Zymomonas mobilis," J. Bacteriol. 174:4504–4508.

Allen, S. P., J. O. Polazzi, J. K. Gierse, A. M. Easton (1992) "Two novel heat shock genes encoding proteins produced in response to heterologous protein expression in Escherichia coli," J. Bacteriol. 174:6938–6947.

An, H., R. K. Scopes, M. Rodriguez, K. F. Keshav, L. O. Ingram (1991) "Gel electrophoretic analysis of Zymomonas mobilis glycolytic and fermentative enzymes: identification of alcohol dehydrogenase II as a stress protein," J. Bacteriol. 173:5975–5982.

Baird, S. D., D. A. Johnson, V. L. Seligy (1990) "Molecular cloning, expression, and characterization of endo-β-1,4-glucanase genes from Bacillus polymyxa and Bacillus circulans," J. Bacteriol. 172:1576–1586.

Beall, D. S., L. O. Ingram (1993) "Genetic engineering of soft-rot bacteria for ethanol production from lignocellulose," J. Ind. Microbiol. 11:151–155.

Brigidi, P., E. De Rossi, M. L. Bertarini, G. Riccardi, D. Matteuzzi (1990) Genetic transformation of intact cells of Bacillus subtilis by electroporation," FEMS Microbiol. Lett. 67:135–138.

Claus, D., R. C. W. Berkeley (1986) "Genus Bacillus Cohn 1872." In Bergey's manual of systematic bacteriology, Vol. 2, Sneath, P. H. A., N. S. Mair, M. E. Sharpe, J. G. Holt (eds), Baltimore: Williams & Wilkins, pp. 1105–1139.

Conway, T., Y. A. Osman, J. I. Konnan, E. M. Hoffman, L. O. Ingram (1987) "Promoter and nucleotide sequence of the Zymomonas mobilis pyruvate decarboxylase," J. Bacteriol. 169:949–954.

Coughlan, M. P., F. Mayer (1991) Chapter 20. "The cellulose-decomposing bacteria and their enzyme system," In Balows, A., H. G. Truper, M. Dworkin, W. Harder, K.-H. Schleifer (eds.) The Procaryotes, Vol. 1, 2nd Edition, New York, Heidelberg, Berlin: Springer-Verlag, pp. 460–516.

Duvall, E. J., D. M. Williams, P. S. Lovett, C. Rudolph, N. Vasantha, M. Guyer (1983) "Chloramphenicol-inducible gene expression in Bacillus subtilis," Gene 24:171–177.

Gong, C.-S., L.-F. Chen, M. C. Flickinger, L.-C. Chiang, G. T. Tsao (1981) Appl. Environ. Microbiol. 41:430.

Harwood, C. R., S. M. Cutting (1991) Molecular biological methods for Bacillus, 1nd edn. West Sussex, England: John Wiley & Sons.

Ingram, L. O., T. Conway (1988) "Expression of different levels of ethanologenic enzymes from Zymomonas mobilis in recombinant strains of E. coli," Appl. Environ. Microbiol. 54:397–404.

Koide, Y., A. Nakamura, T. Uozumi, T. Beppu (1986) "Cloning and sequencing of the major intracellular serine protease gene of Bacillus subtilis," J. Bacteriol. 167:110–116.

Laemmli, U. K. (1970) "Cleavage of structural proteins during the assembly of the head of bacteriophage T4," Nature 227:680–685.

Lee et al. (1992) "Effect of overproduction of heat shock chaperones GroESL and DnaK on human collagenase production in *Escherichia coli*," *Biol. Chem.* 267:28849–2852.

Luria, S. E., M. Delbruck (1943) "Mutations of bacteria from virus sensitivity to virus resistance," *Genetics* 28:491–511.

Mistry, F. R., C. L. Cooney (1989) "Production of ethanol by *Clostridium thermosaccharolyticum*: I. Effect of cell recycle and environmental parameters," *Biotechnol. Bioeng.* 34:1295.

Mistry, F. R., C. L. Cooney (1989) "Production of ethanol by *Clostridium thermosaccharolyticum*: II. A quantitative model describing product distributions," *Biotechnol. Bioeng.* 34:1305.

O'Hara, M. B., J. H. Hageman (1990) "Energy and calcium ion dependence of proteolysis during sporulation of *Bacillus subtilis* cells," *J. Bacteriol.* 172:4161–4170.

Sambrook, J., E. F. Fritsch, T. Maniatis (1989) *Molecular cloning: a laboratory manual*, 2nd edn., Cold Spring Harbor Laboratory, Cold Spring Harbor, N.Y.

Sarthy, A. V., B. L. McConaughy, Z. Lobo, J. A. Sundstrom, C. E. Furlong, B. D. Hall (1987) *Appl. Environ. Microbiol.* 53:1996.

Schoner, R. G., D. M. Williams, P. S. Lovett (1983) "Enhanced expression of mouse dihydrofolate reductase in *Bacillus subtilis*," *Gene* 22:47–57.

Slepecky, R. A., H. E. Hemphill (1991) Chapter 76. "The genus Bacillus-nonmedical," In Balows, A., H. G. Truper, M. Dworkin, W. Harder, K.-H. Schleifer (eds.) *The Procaryotes,* Vol. 1, 2nd Edition, New York, Heidelberg, Berlin: Springer-Verlag, pp. 1663–1696.

Williamson, V. M., J. Bennetzen, E. T. Young (1980) "Isolation of the structural gene for alcohol dehydrogenase by genetic complementation in yeast," *Nature* 283:214–216.

Wood, B. E., L. O. Ingram (1992) "Ethanol production from cellobiose, amorphous cellulose and crystalline cellulose by recombinant strains of *Klebsiella oxytoca* containing chromosomally integrated *Zymomonas mobilis* genes for ethanol production and plasmids expressing thermostable cellulase genes from *Clostridium thermocellum*," *Appl. Environ. Microbiol.* 58:2103–2110.

Yasbin, R. E., P. I. Fields, B. J. Anderson (1980) "Properties of *Bacillus subtilis* 168 derivatives freed of their natural prophages," *Gene* 12:155–159.

Zehender, H., D. Trescher, J. Ullrich (1983) "Activity strain for pyruvate decarboxylase in polyacrylamide gels," *Anal. Biochem.* 135:16–21.

We claim:

1. A Gram-positive bacterium which has been transformed with heterologous genes encoding alcohol dehydrogenase and pyruvate decarboxylase wherein said genes are expressed at sufficient levels to confer upon said Gram-positive bacterium transformant the ability to produce ethanol as a fermentation product.

2. The Gram-positive bacterium, according to claim 1, wherein said host is selected from the group consisting of Bacillus, Lactobacillus, Streptococcus, Fibribacter, Ruminococcus, Pediococcus, Cytophaga, Cellulomonas, Bacteroides, and Clostridium.

3. The Gram-positive bacterium according to claim 2, wherein said host is a Bacillus sp.

4. The Gram-positive bacterium, according to claim 3, wherein said Bacillus sp. is selected from the group consisting of *B. subtilis* and *B. polymyxa*.

5. The Gram-positive bacterium, according to claim 1, which has been transformed with *Z. mobilis* genes encoding alcohol dehydrogenase and pyruvate decarboxylase.

6. The Gram-positive bacterium according to claim 1, wherein said bacterium is further transformed with a gene encoding an enzyme which degrades oligosaccharides.

7. The Gram-positive bacterium, according to claim 6, wherein said enzyme which degrades oligosaccharides is a polysaccharase.

8. The Gram-positive bacterium according to claim 7, wherein said polysaccharase is selected from the group consisting of cellulolytic, xylanolytic, and starch-degrading enzymes.

9. The Gram-positive bacterium, according to claim 1, wherein said heterologous genes are incorporated onto the chromosome of said bacterium.

10. A method for the production of ethanol, said method comprising transforming a Gram-positive bacterial host with heterologous genes encoding pyruvate decarboxylase and alcohol dehydrogenase wherein said genes are expressed at sufficient levels to result in the production of ethanol as a fermentation product.

11. The method, according to claim 10, wherein said host is selected from the group consisting of Bacillus, Lactobacillus, Streptococcus, Fibribacter, Ruminococcus, Pediococcus, Cytophaga, Cellulomonas, Bacteroides, and Clostridium.

12. The method, according to claim 11, wherein said host is a Bacillus sp.

13. The method, according to claim 12, wherein said Bacillus sp. is selected from the group consisting of *B. subtilis* and *B. polymyxa*.

14. The method, according to claim 10, wherein said Gram-positive bacterium has been transformed with *Z. mobilis* genes encoding alcohol dehydrogenase and pyruvate decarboxylase.

15. The method, according to claim 10, wherein said bacterium is further transformed with a gene encoding an enzyme which degrades oligosaccharides.

16. The method, according to claim 15, wherein said enzyme which degrades oligosaccharides is a polysaccharase.

17. A method for reducing the accumulation of acidic metabolic products in the growth medium of Gram-positive bacteria, said method comprising transforming said bacteria with heterologous genes which express alcohol dehydrogenase and pyruvate decarboxylase at sufficient levels to result in the production of ethanol as a fermentation product.

18. A plasmid designated pLOI1500.

* * * * *

UNITED STATES PATENT AND TRADEMARK OFFICE
CERTIFICATE OF CORRECTION

PATENT NO. : 5,916,787  Page 1 of 1
APPLICATION NO. : 08/475925
DATED : June 29, 1999
INVENTOR(S) : Lonnie O. Ingram et al.

It is certified that error appears in the above-identified patent and that said Letters Patent is hereby corrected as shown below:

At Column 1, Line 26, after the period following the word "Energy" please add the following sentence:

--The Government has certain rights in the invention.--

Signed and Sealed this

Seventh Day of August, 2007

JON W. DUDAS
*Director of the United States Patent and Trademark Office*